US010083543B2

United States Patent
Yang et al.

(10) Patent No.: US 10,083,543 B2
(45) Date of Patent: Sep. 25, 2018

(54) METAL ARTIFACTS REDUCTION FOR CONE BEAM CT USING IMAGE STACKING

(71) Applicant: Carestream Dental Technology Topco Limited, London (GB)

(72) Inventors: Dong Yang, Rochester, NY (US); Lawrence A. Ray, Rochester, NY (US); Andre Souza, Webster, NY (US); Alexandre X. Falcao, Rochester, NY (US)

(73) Assignee: Carestream Dental Technology Topco Limited, London (GB)

( * ) Notice: Subject to any disclaimer, the term of this patent is extended or adjusted under 35 U.S.C. 154(b) by 0 days.

(21) Appl. No.: 14/576,264

(22) Filed: Dec. 19, 2014

(65) Prior Publication Data

US 2015/0178917 A1     Jun. 25, 2015

Related U.S. Application Data

(60) Provisional application No. 61/919,005, filed on Dec. 20, 2013.

(51) Int. Cl.
*G06T 17/00* (2006.01)
*G06T 11/00* (2006.01)
(Continued)

(52) U.S. Cl.
CPC .............. *G06T 17/00* (2013.01); *A61B 6/032* (2013.01); *A61B 6/4085* (2013.01);
(Continued)

(58) Field of Classification Search
None
See application file for complete search history.

(56) References Cited

U.S. PATENT DOCUMENTS

| 5,270,926 A | 12/1993 | Tam |
| 5,999,587 A | 12/1999 | Ning et al. |

(Continued)

OTHER PUBLICATIONS

Chen et al., "CT Metal Artifact Reduction Method Based on Improved Image Segmentation and Sinogram In-Painting," Mathematical problems in Engineering, vol. 2012, Article ID 786281.*

(Continued)

*Primary Examiner* — Matthew Bella
*Assistant Examiner* — Soo Shin

(57) ABSTRACT

Method and/or apparatus embodiments can process volume image data of a subject. An exemplary method includes obtaining a first group of two-dimensional radiographic images of the subject, wherein each of the images is obtained with a detector and a radiation source at a different scan angle. The method arranges image data from the first group of images in an image stack so that corresponding pixel data from the detector is in register for each of the images in the image stack. Pixels that represent metal objects are segmented from the image stack and data replaced for at least some of the segmented pixels to generate a second group of modified two-dimensional radiographic images. The second group of images is combined with the first group to generate a three-dimensional volume image according to the combined images and an image slice from the three-dimensional volume image is displayed.

14 Claims, 8 Drawing Sheets

(51) Int. Cl.
*G06T 5/00* (2006.01)
*A61B 6/03* (2006.01)
*A61B 6/00* (2006.01)

(52) U.S. Cl.
CPC ............ *A61B 6/5258* (2013.01); *G06T 5/005* (2013.01); *G06T 11/005* (2013.01); *G06T 2207/10081* (2013.01); *G06T 2207/30052* (2013.01)

(56) References Cited

U.S. PATENT DOCUMENTS

| | | | | |
|---|---|---|---|---|
| 8,582,855 | B2* | 11/2013 | Koehler | G06T 11/005 382/131 |
| 9,202,296 | B2* | 12/2015 | Yang | G06T 11/008 |
| 2010/0183214 | A1* | 7/2010 | McCollough | A61B 6/032 382/131 |
| 2011/0044546 | A1* | 2/2011 | Pan | G06T 11/006 382/195 |
| 2011/0081071 | A1* | 4/2011 | Benson | G06T 11/005 382/154 |
| 2011/0150307 | A1* | 6/2011 | Souza | G06T 5/002 382/131 |
| 2013/0070991 | A1 | 3/2013 | Yang et al. | |
| 2016/0078647 | A1* | 3/2016 | Schildkraut | G06T 11/005 382/131 |

OTHER PUBLICATIONS

Mehranian et al., "3D Prior Image Constrained Projection Completion for X-ray CT Metal Artifact Reduction," IEEE Transactions on Nuclear Science, vol. 60, No. 5, Oct. 2013.*
Scarfe et al. "What is Cone-Beam CT and How Does it Work?" Dent Clin N Am, vol. 52 (2008), pp. 707-730.*
L. A. Feldkamp, et al., "Practical Cone-Beam Algorithm", Optical Society of America, 1984, vol. 1, No. 6, pp. 612-619.
Willi A. Kalender, et al., "Reduction of CT Artifacts Caused by Metallic Implants", Radiology, 1987, pp. 576-577.
Marcelo Bertalmio, et al., "Image Inpainting", Conference on Computer Graphics and Interactive Techniques, 2000, pp. 1-8.
Alexandre X. Falcao, et al., "The Image Foresting Transform: Theory, Algorithms, and Applications", IEEE, 2004, vol. 26, No. 1, pp. 19-29.
Rezvani, "Reconstruction Algorithms in Computerized Tomography", CAIMS (Canadian Applied and Industrial Mathematics Society) 2009, The University of Western Ontario, Jun. 2009 (.g., see slides 7-19 for an overview of reconstruction techniques).
Scherl et al., "Implementation of the FDK algorithm for cone-beam CT on the cell broadband engine architecture", Proceedings vol. 6510, Medical Imaging 2007, Physics of Medical Imaging (see Section 3. Method and Section 4. Implementation on pp. 2-5 (e.g., discussing FDK algorithm)).

* cited by examiner

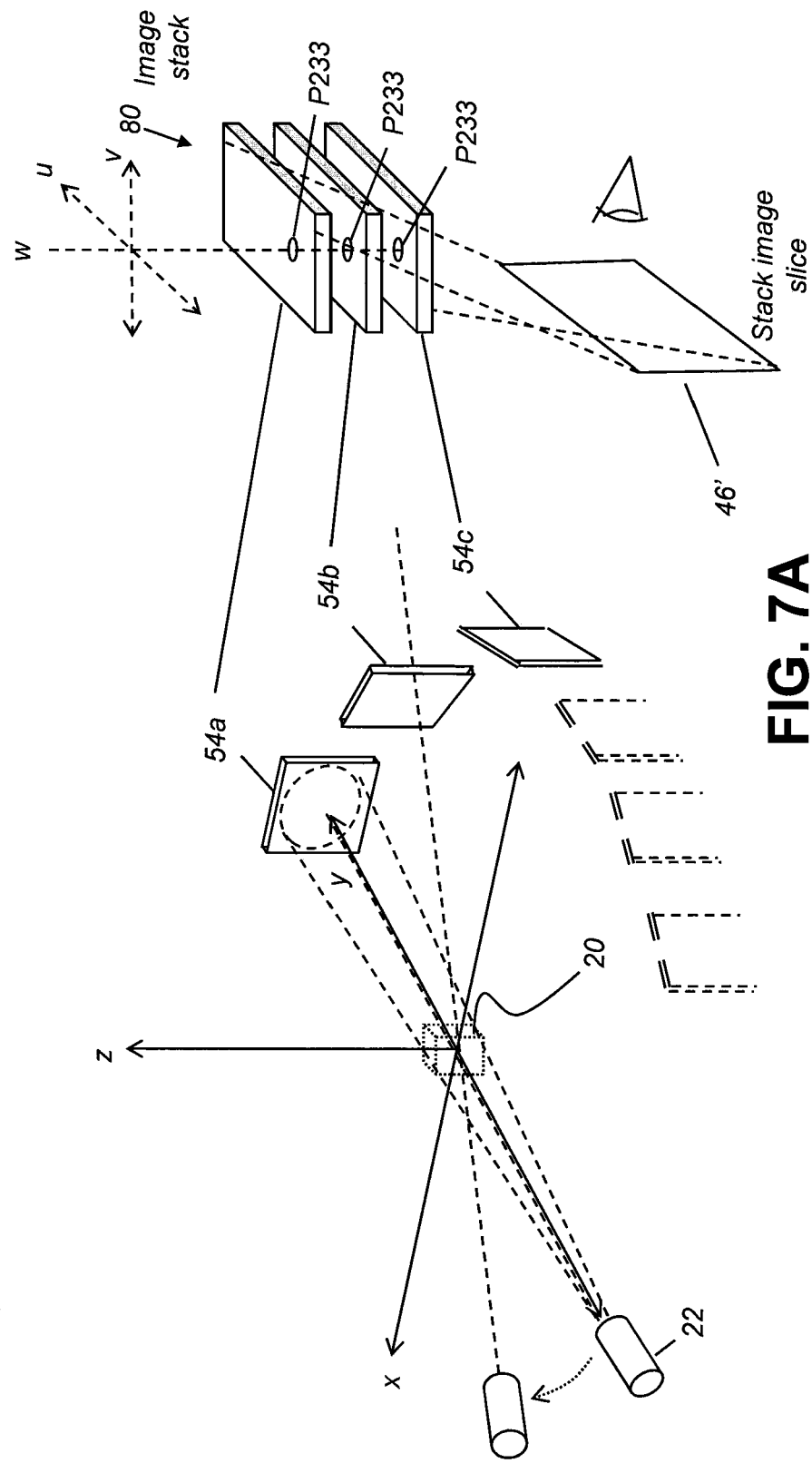

METAL ARTIFACTS REDUCTION FOR CONE BEAM CT USING IMAGE STACKING

CROSS REFERENCE TO RELATED APPLICATIONS

This application claims the benefit of U.S. Provisional application U.S. Ser. No. 61/919,005 provisionally filed on Dec. 20, 2013, entitled "METAL ARTIFACTS REDUCTION FOR CONE BEAM CT USING IMAGE STACKING", in the names of Dong YANG et al., which is incorporated herein by reference in its entirety.

FIELD OF THE INVENTION

The disclosure relates generally to the field of diagnostic imaging and in particular to Cone-Beam Computed Tomography (CBCT) imaging. More specifically, the disclosure relates to a method for improving CBCT results using segmentation techniques to reduce metal artifacts in the reconstructed image.

BACKGROUND OF THE INVENTION

3-D volume imaging can be a diagnostic tool that offers advantages over earlier 2-D radiographic imaging techniques for evaluating the condition of internal structures and organs. 3-D imaging of a patient or other subject has been made possible by a number of advancements, including the development of high-speed imaging detectors, such as digital radiography (DR) detectors that enable multiple images to be taken in rapid succession.

Cone beam computed tomography (CBCT) or cone beam CT technology offers considerable promise as one type of diagnostic tool for providing 3-D volume images. Cone beam CT systems capture volume data sets by using a high frame rate flat panel digital radiography (DR) detector and an x-ray source, typically affixed to a gantry that revolves about the object to be imaged, directing, from various points along its orbit around the subject, a divergent cone beam of x-rays toward the subject. The CBCT system captures projection images throughout the source-detector orbit, for example, with one 2-D projection image at every degree increment of rotation. The projections are then reconstructed into a 3-D volume image using various algorithmic techniques. Among the methods for reconstructing the 3-D volume image are filtered back projection (FBP) approaches. An exemplary reconstruction approach is described, for example, in the paper by L. A. Feldkamp, L. C. Davis, and J. W. Kress, entitled "Practical cone-beam algorithm," *Journal of the Optical Society of America*, vol 1, pp. 612-619, June, 1984.

Although 3-D images of diagnostic quality can be generated using CBCT systems and technology, technical challenges remain. Highly dense objects, such as metallic implants, prostheses and related appliances, surgical clips and staples, dental fillings, and the like can cause various image artifacts that can obscure useful information about the imaged tissue. This occurs because dense objects having a high atomic number attenuate X-rays in the diagnostic energy range much more strongly than do soft tissue or bone features. When dense structures are in the exposure path, fewer photons reach the imaging detector through these objects. For 3-D imaging, the image artifacts that can be generated in reconstruction routines by metallic and other highly dense objects include dark and/or bright streaks that spread across the entire reconstructed image. Such artifacts can be due to physical effects such as high quantum noise, radiation scatter, beam hardening, and/or non-linear amplification in reconstruction algorithms. These artifacts, generically referred to metallic artifacts or metal artifacts, can reduce image quality by masking soft tissue structures, not only in the immediate vicinity of the dense object, but also throughout the entire image. Without some type of compensation, metal artifacts in 3-D volumes can falsify CT values and even make it difficult or impossible to use the reconstructed image effectively in assessing patient condition or properly planning radiation therapy or other treatments.

Approaches have been tried for metal artifacts reduction (MAR), including: 1. Interpolation-based FBP reconstruction approach; 2. Iterative reconstruction approach; and 3. Quasi-iterative based FBP approach.

An exemplary MAR approach is described, for example, by W. A. Kalender, R. Hebele, and J. Ebersberger, in an article entitled "Reduction of CT artifacts caused by metallic implants", *Radiology* 164(2), 576{577 (1987).

It is recognized that metal artifacts reduction is a challenging task, particularly where implant geometries may be more complex. There is a need for metal artifacts reduction that offer improved performance and/or computational efficiency.

SUMMARY OF THE INVENTION

An aspect of this application is to advance the art of medical diagnostic imaging, particularly for dental applications.

Another aspect of this application is to address, in whole or in part, at least the foregoing and other deficiencies in the related art.

It is another aspect of the application to provide, in whole or in part, at least the advantages described herein.

It is an object of the application to advance the art of volume imaging and provide improved ways to reduce metal artifacts in CBCT volume images. Certain exemplary apparatus and/or method embodiments can be configured to act or operate in the projection domain, thereby improving the overall efficiency of the process and/or reducing computational demands.

According to one aspect of the invention, there is provided a method for processing volume image data of a subject that can include obtaining two-dimensional radiographic images of the subject on an image detector, where the two-dimensional radiographic images are obtained with the detector and a radiation source at a different scan angle relative to the subject; arranging the image data from a first plurality of two-dimensional radiographic images in an image stack so that corresponding pixel data from the detector is in register for each of the images in the image stack; segmenting pixels that represent metal objects from the image stack; replacing data for at least some of the segmented pixels to generate a second plurality of modified two-dimensional radiographic images; combining the second plurality of modified two-dimensional radiographic images with the first plurality of two-dimensional radiographic images of the subject to form a third plurality of corrected two-dimensional radiographic images; generating a three-dimensional volume image according to the third plurality of corrected two-dimensional radiographic images; and displaying, storing, or transmitting an image slice from the three-dimensional volume image.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIGS. 7A-7B are diagrams that shows exemplary stack image slices that pass though at least some of the arrangement of projection images in an image stack according to various selected embodiments of the application.

DESCRIPTION OF EXEMPLARY EMBODIMENTS

Figure 1:
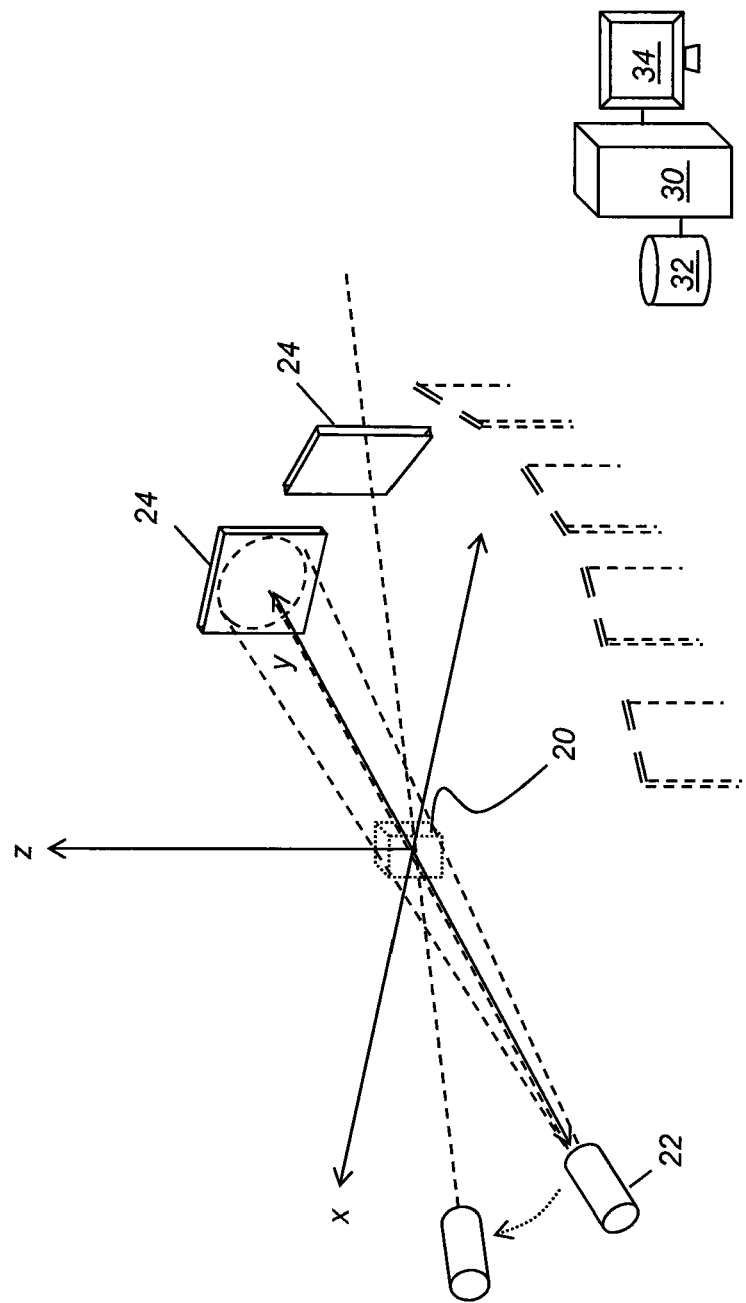
FIG. 1 is a block diagram schematic of a CBCT apparatus that shows exemplary operations to obtain 2-D projection images used to generate 3-d volume images or 3-D reconstructions.

The following is a description of exemplary embodiments, reference being made to the drawings in which the same reference numerals identify the same elements of structure in each of the several figures.

In the drawings and text that follow, like components are designated with like reference numerals, and similar descriptions concerning components and arrangement or interaction of components already described are omitted. Where they are used, the terms "first", "second", "third", and so on, do not necessarily denote any ordinal or priority relation, but are simply used to more clearly distinguish one element from another.

In the context of the application, the term "volume image" is synonymous with the terms "3-dimensional image" or "3-D image". Certain exemplary apparatus and/or method embodiments according to the application are particularly well suited for suppressing various types of metal artifacts that occur in 3-D volume images, including but not limited to cone-beam computed tomography (CBCT) as well as fan-beam CT images. However, it should be noted that various artifacts reduction methods and/or apparatus embodiments described herein may also be applicable for 2-D radiographic images, as described in more detail subsequently.

For the image processing steps described herein, the terms "pixels" and "pixel data" for picture image data elements, conventionally used with respect 2-D imaging and image display, and "voxels" for volume image data elements, often used with respect to 3-D imaging, can be used interchangeably. It should be noted that the 3-D volume image is itself synthesized from image data obtained as pixels on a 2-D sensor array and displays as a 2-D image from some angle of view. Thus, 2-D image processing and image analysis techniques can be applied to the 3-D volume image data. In the description herein, techniques described as operating upon pixels may alternately be described as operating upon the 3-D voxel data that is stored and represented in the form of 2-D pixel data for display. In the same way, techniques that operate upon voxel data can also be described as operating upon pixels.

In the context of the application, high-density objects that cause what is commonly known as metal artifacts in the volume image are termed "metal" objects. This includes objects formed from materials having a relatively high mass attenuation coefficient. The mass attenuation coefficient for a material is not a fixed value, but varies, dependent, in part, on the photon energy level. An exemplary metal object of titanium, for example, has a mass attenuation coefficient of 4.972 $cm^2/g$ at 30 keV and a mass attenuation coefficient of 0.4052 $cm^2/g$ at 80 keV. Any object having attenuation at or near that of titanium or higher can be considered to be a metal object. It should be noted, for example, that objects formed from some types of highly dense composite materials can have a similar effect on image quality. Exemplary apparatus and/or method embodiments of the application address the type of artifact generated by such an object, of whatever material type or other composition. Materials commonly used and known to cause at least some type of "metal artifact" in radiographs and volume images include metals such as iron, cobalt, chromium, titanium, tantalum, and alloys including cobalt chromium alloys, for example, as well as some ceramic compositions and various composite materials such as high density composite plastics.

CBCT imaging apparatus and the imaging algorithms used to obtain 3-D volume images using such systems are well known in the diagnostic imaging art and are, therefore, not described in detail in the present application. Some exemplary algorithms and approaches for forming 3-D volume images from the source 2-D projection images that are obtained in operation of the CBCT imaging apparatus can be found, for example, in the Feldkamp et al. paper noted previously and in U.S. Pat. No. 5,999,587 entitled "Method of and System for Cone-Beam Tomography Reconstruction" to Ning et al. and U.S. Pat. No. 5,270,926 entitled "Method and Apparatus for Reconstructing a Three-Dimensional Computerized Tomography (CT) Image of an Object from Incomplete Cone Beam Data" to Tam.

In typical applications, a computer or other type of dedicated logic processor for obtaining, processing, and storing image data is part of the CBCT system, along with one or more displays for viewing image results. A computer-accessible memory is also provided, which may be a memory storage device used for longer term storage, such as a device using magnetic, optical, or other data storage media. In addition, the computer-accessible memory can comprise an electronic memory such as a random access memory (RAM) that is used for shorter term storage, such as employed to store a computer program having instructions for controlling one or more computers to practice or instantiate certain exemplary apparatus and/or method embodiments according to the application.

It is instructive to describe principles and terminology used for CBCT image capture and reconstruction. Referring to the perspective view of FIG. 1, there is shown, in schematic form and using enlarged distances for clarity of description, the activity of a conventional CBCT imaging apparatus for obtaining the individual 2-D images that are used to form a 3-D volume image. A cone-beam radiation source 22 directs a cone of radiation toward a subject 20, such as a patient or other subject in an imaging area between the source 22 and a DR detector 24. A sequence of images is obtained in rapid succession at varying angles about the subject, such as one image at each 1-degree angle increment along a circular arc greater than 180 degrees. The DR detector 24 is moved to different imaging positions about subject 20 in concert with corresponding movement of radiation source 22. Each individual projection image is obtained in its respective XY plane, using Cartesian coordinate designations for the detector 24.

FIG. 1 shows a representative sampling of DR detector 24 positions to illustrate how the projection images are obtained relative to the position of subject 20. Such corresponding movements of the source 22 and the detector 24 in obtaining the plurality of projection images (e.g., raw projection images) can be called a scan. Exemplary scans can use various 2-D and/or 3-D patterns around the imaging area or portion thereof. Once sufficient 2-D projection images are captured in this sequence, a suitable reconstruction algorithm, such as filtered back projection (FBP), is used for generating the 3-D volume image. Image acquisition and program execution are performed by a computer 30 (e.g., local or remote) or by a networked group of computers 30 that are in image data communication with DR detectors 24. Image processing and storage is performed using a computer-accessible memory 32. The generated 3-D volume image can be presented on a display 34, stored and/or transmitted remotely.

FBP is a discrete implementation of a simple analytic model that assumes that CT transmission measurements are linear functions of the attenuation line integrals along the corresponding primary photon trajectories through the subject and are noiseless. When scanning subjects comprised of only anatomically native materials under normal conditions, relatively simple corrections to the raw projection data are sufficient to assure that these assumptions (e.g., linear relationship) are at least approximately valid. This treatment typically allows images that are free of visually observable artifacts. However, in regions shadowed by highly dense, attenuating objects such as metal, there can be a dramatic increase in noise and/or nonlinear detector response due to scatter and/or beam hardening, which can individually or in combination, give rise to pronounced streaking artifacts. Mismatches between the simple FBP model of detector response and the physical process of signal acquisition when metal objects are in the scanning field of view are a significant source of those metal artifacts. An accurate physical model of the CT signal acquisition process is useful to mitigate the metal artifacts based on FBP reconstruction.

Figure 2:
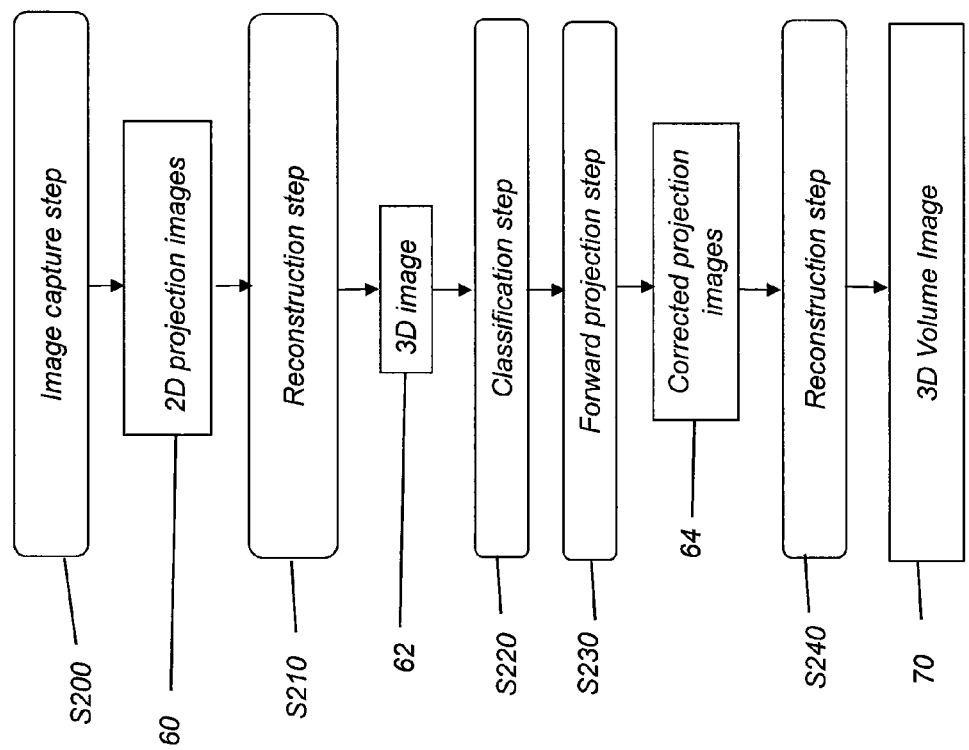
FIG. 2 is a logic flow diagram that shows a conventional sequence for metal artifacts reduction in volume reconstruction.

The logic flow diagram of FIG. 2 shows an image processing sequence that is conventionally used for metal artifacts reduction, as described previously in the background section. In an image capture step S200, a complete set of projection images 60 is obtained. Reconstruction, such as FBP reconstruction, is then used in a reconstruction step S210 to generate a 3-D image 62. Then, a classification step S220 executes, classifying each voxel in the reconstruction as metal or bone/tissue. This information is used for forward projection in a forward projection step S230 to generate a corrected set of projection images 64. A second reconstruction step S240 executes, generating a 3-D image 70 for display with reduced metal artifacts.

The method described with reference to FIG. 2 provides some image correction. However, its repeated reconstruction processing is computer-intensive and can take a significant amount of time.

Figure 3:
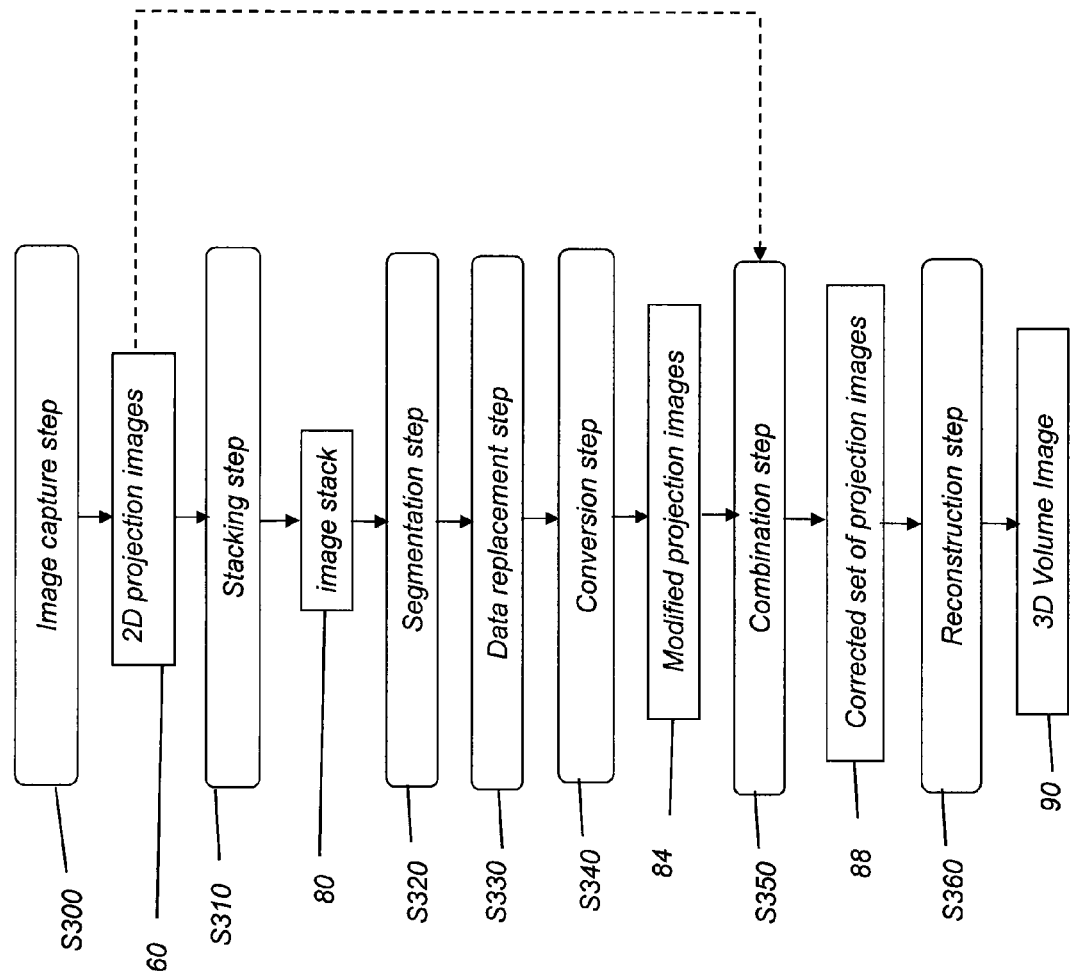
FIG. 3 is a logic flow diagram that shows a sequence for metal artifacts reduction in volume reconstruction according to an exemplary embodiment of the present disclosure.

In view of what is needed for metal artifacts reduction, and to provide improved results and/or improved computational efficiency over conventional processing methods, Applicants have variously employed a different metal artifact reduction approach. The logic flow diagram of FIG. 3 shows an exemplary image processing sequence for 3-D volume image reconstruction with compensation for metal artifacts according to an embodiment of the application. In an image capture step S300, complete set of projection images 60 is obtained. A stacking step S310 is then executed, stacking the projection images, in order to form an image stack 80, described in more detail subsequently. A segmentation step S320 is executed on image stack 80 to segment the metal object from tissue in the imaged subject. A data replacement step S330 is then executed to replace segmented data identified as metal. A conversion step S340 then converts the data obtained from processing the image stack 80 to generate a modified second set of projection images 84. A combination step S350 then combines pixel data from the corrected set of projection images 84 with the original set of projection images 60 to generate a corrected third set of projection images 88. A reconstruction step S360 is then executed, using the third corrected set of projection images 88 to generate a 3-D image 90 with reduced metal artifacts. The reconstructed 3-D image 90 can be displayed, stored, or transmitted. Two-dimensional slices of the generated 3-D volume image are then displayed on display 34 (FIG. 1). Individual steps in this FIG. 3 sequence are described in more detail subsequently.

Stacking Step S310

In stacking step S310 of the FIG. 3 sequence, the projection images, each in its XZ or coronal plane at the angle of image capture on detector 24, as shown in FIG. 1, are stacked so that corresponding pixels within each image are in register. In this stacking, for example, pixels having the same coordinates are aligned in register with each other. The projection images from different angles or views are stacked in register, corresponding to each of the successive scanning view angles.

Figure 4:
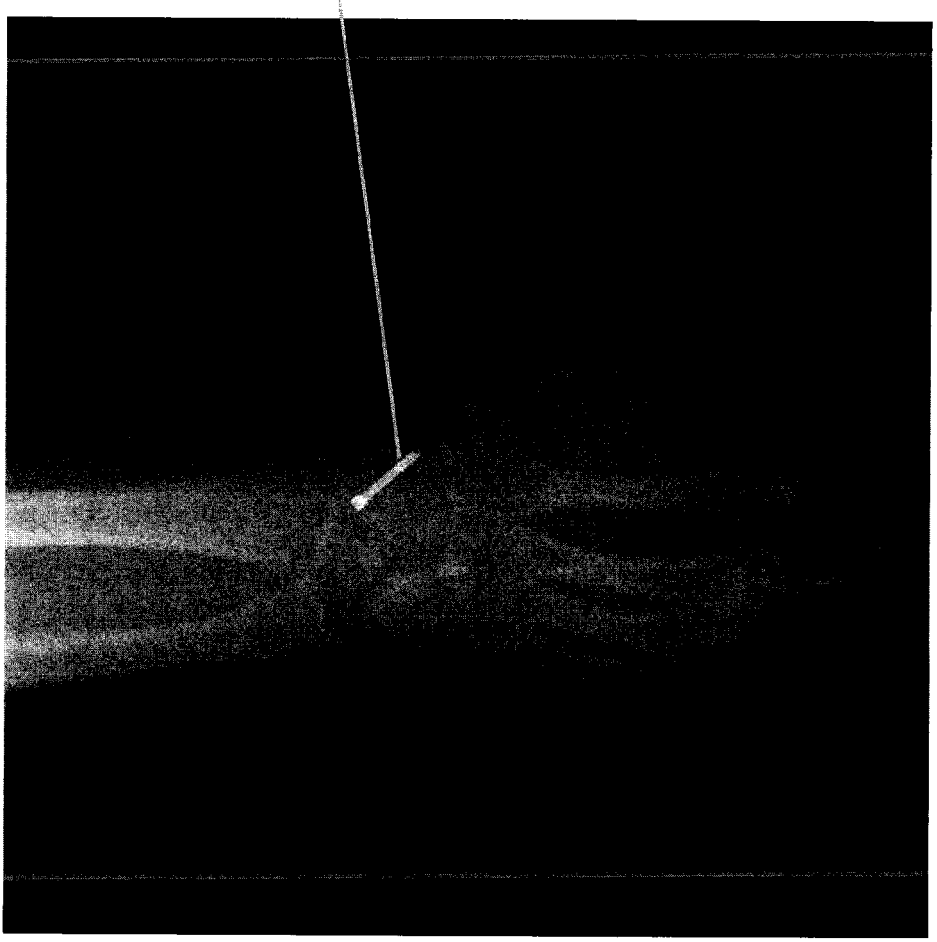
FIG. 4 is a diagram that shows an image slice for anatomy having a metal object from a reconstructed 3-D volume.
Figure 5:
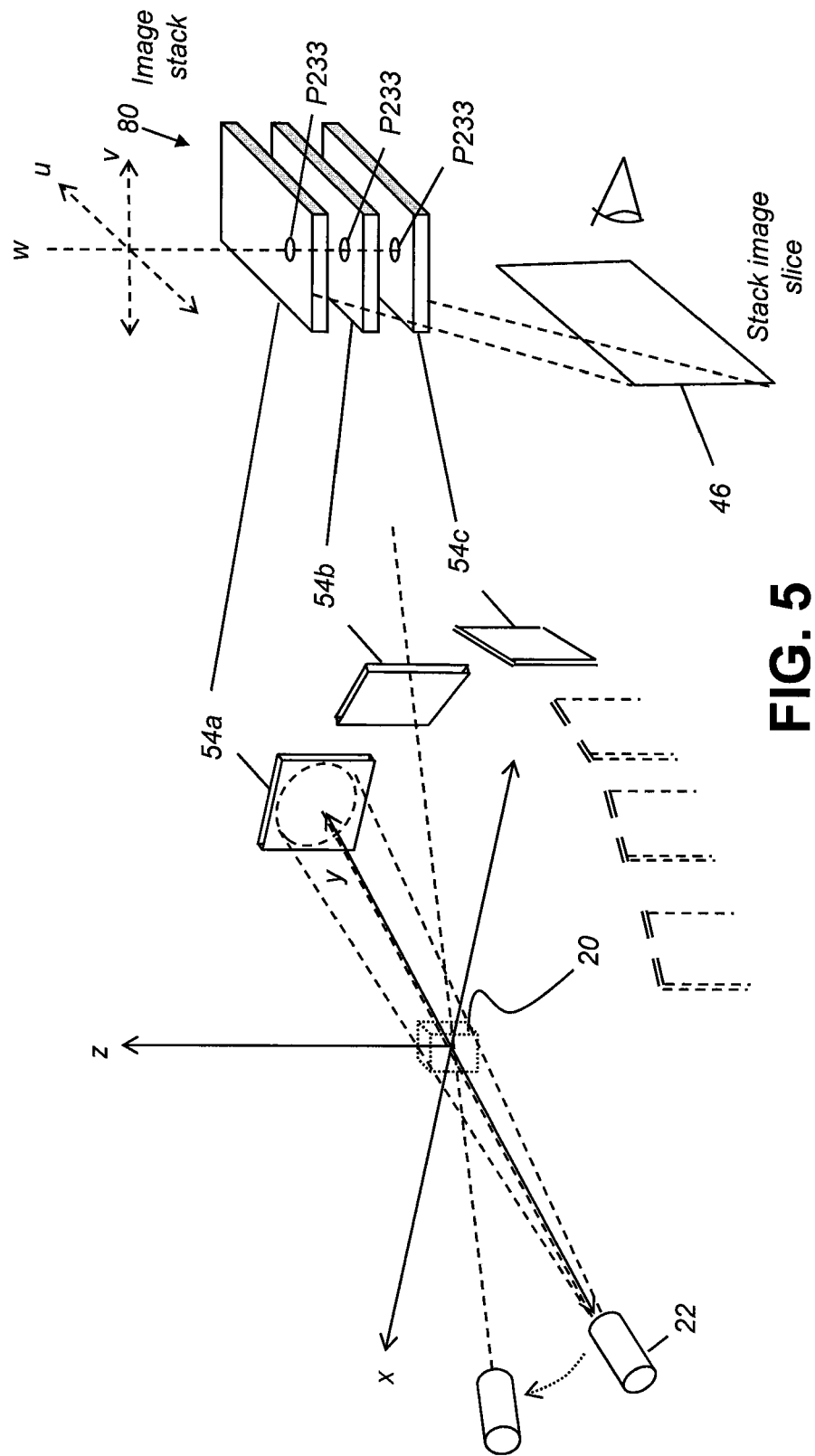
FIG. 5 is a diagram that shows an exemplary stacking arrangement of projection images used according to an embodiment of the application.

The stacking arrangement that is used processes image content from an angle that is orthogonal to the axis of the radiation beam. By way of example, FIG. 4 shows an image slice 44 from a reconstructed volume that contains a metal object 28, such as an insert. FIG. 5 illustrates the stacking arrangement relative to the image acquisition scan, in schematic form, simplified for clarity to show only three stacked projection images 54a, 54b, and 54c in image stack 80. In practice, several hundred projection images would be in an image stack 80. It must be emphasized that image stack 80 is not a reconstructed volume that is formed by processing the projection image pixels to provide voxel values; image stack 80 is simply a representative grouping of data formed by stacking successive images so that their respective pixels are in register. That is, corresponding pixel data from the detector 24 (FIG. 1) is in register for each of the projection images 54a, 54b, 54c, and so on, in the image stack. Relative to the image detector 24, the coordinates (u, v) for each pixel in the stacked projection images 54a, 54b, and 54c are aligned with each other in the image stack arrangement.

As shown in the FIG. 5 example, a representative pixel P233 on projection image 54a is in register with pixel P233 on projection images 54b and 54c. According to an embodiment of the application, slices 46 from this image stack are taken in a direction orthogonal to the uv plane that is shown and are viewed from along the v axis direction or parallel to the v axis direction. This process keeps track of the original (u, v) coordinates of each pixel as obtained by detector 24 so that the original projection image 54a, 54b, 54c, and so on, can be modified and used in subsequent reconstruction. It can also be appreciated that the slice 46 that is processed can be in the uw plane or parallel to the uw plane, using the axis representation shown in FIG. 5, or in some other plane that is orthogonal to the uv plane. The w axis in FIG. 5 represents the particular view angle of the originally obtained projection image, considered from the perspective of the radiation source 22. Multiple planes are processed so that each pixel in each projection image is processed in one of the image stack slices 46 that are taken from image stack 80. A single stack image slice 46 is represented in FIG. 5 as it would be viewed when considered apart from image stack 80. The term "stack image slice", numbered 46, is preferably used herein to describe a 2-D image slice that is obtained as an orthogonal slice from image stack 80. It can be appreciated that the two-dimensional stack image slice 46 has image pixel data from each of the first plurality of 2-D projection images that were originally obtained. It should also be emphasized that stack image slice 46, an arrangement of pixels taken from image stack 80, is a different type of image slice than the 2-D image slice 44 that is obtained from voxels of the reconstructed volume, such as image slice 44 shown in FIG. 4.

Figure 6:
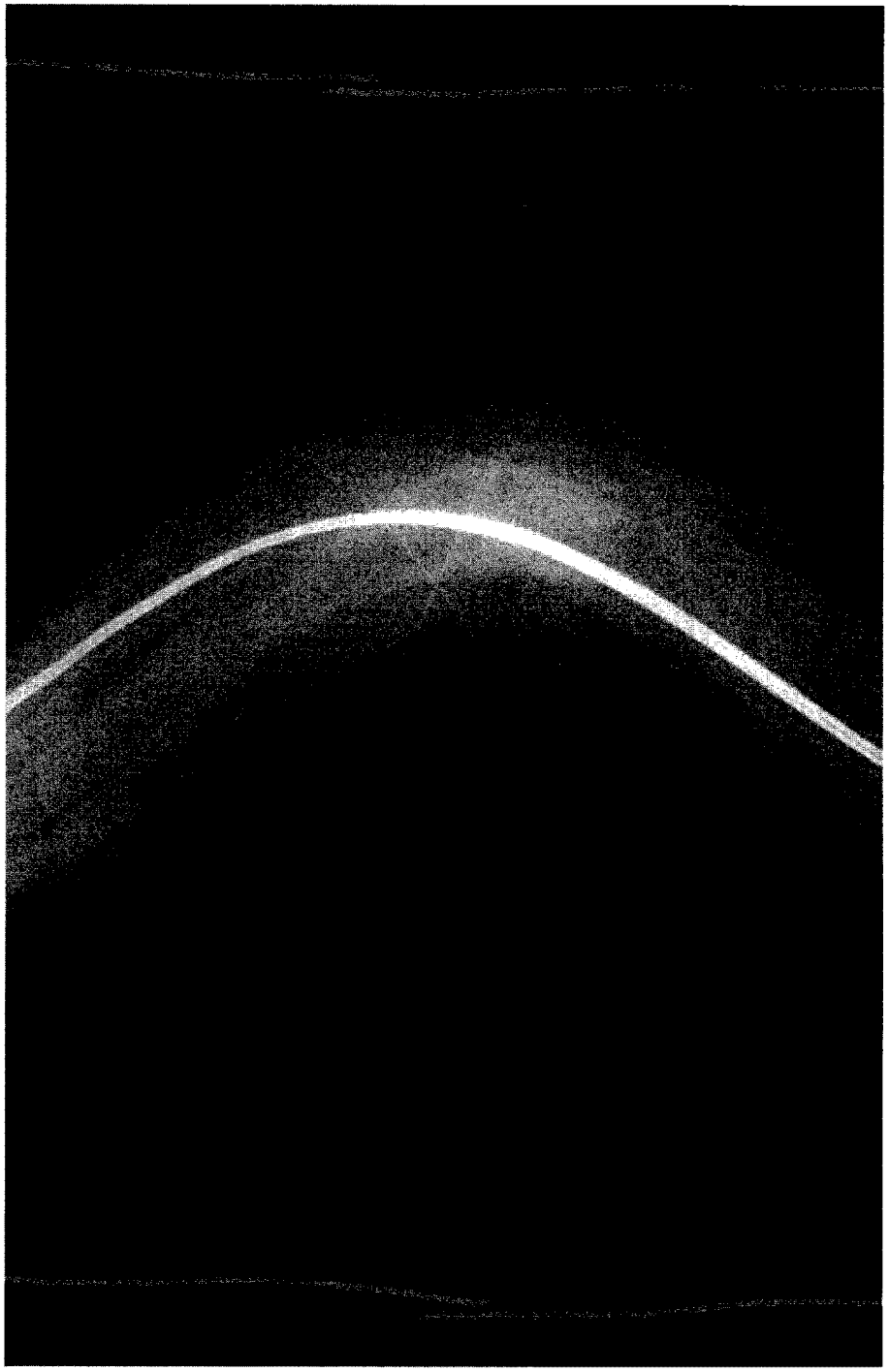
FIG. 6 is a diagram that shows an exemplary slice from the stacked projection images according to an embodiment of the application.

By way of example, FIG. 6 shows a stack image slice 46 obtained from stacked projection images for the anatomy shown in FIG. 4, using the stacking arrangement described with respect to FIG. 5. The characteristic sinusoidal pattern that is obtained from stacking the projection image data in this way can be used to efficiently identify metal and other dense objects and to differentiate these objects from the balance of the imaged anatomy.

In one embodiment, with the images stacked in register in this manner, automatic 3-D metal segmentation can be performed by considering successive sagittal stack image slices 46 through the stack. According to an embodiment of the application, segmentation is conducted in this image stack using an adapted execution of the Image Foresting Transform (IFT). The Image Foresting Transform takes advantage of the capability for expressing a multi-dimensional image as a set of nodes and arc-weights. This is described, for example, in detail in the article entitled "The Image Foresting Transform: Theory, Algorithm, and Applications," in *IEEE Trans on Pattern Analysis and Machine Intelligence*, 26 (1): 19-29, 2004, fully incorporated herein by reference. Using the alternate data representation employed by the IFT, substantial amounts of image data can be efficiently processed at high speed, using techniques familiar to those skilled in the image processing arts.

Within the IFT framework, once all stack image slices 46 are obtained and initially processed, each slice 46 is automatically processed to identify a suitable number of seed pixels. Each seed pixel is unambiguously categorized as skin/body tissue or metal. These seeds are then used to segment the metal feature automatically in the 3-D volume data set in step S320 (FIG. 3), identifying pixels associated with, or very likely to indicate, metal features.

Seed identification for metal and non-metal image components can be performed automatically, such as using information on material density that is obtained from each image projection. According to an alternate embodiment of the application, seeds for IFT processing can be identified manually by the operator using a mouse or other pointing device for input.

Figure 7B:
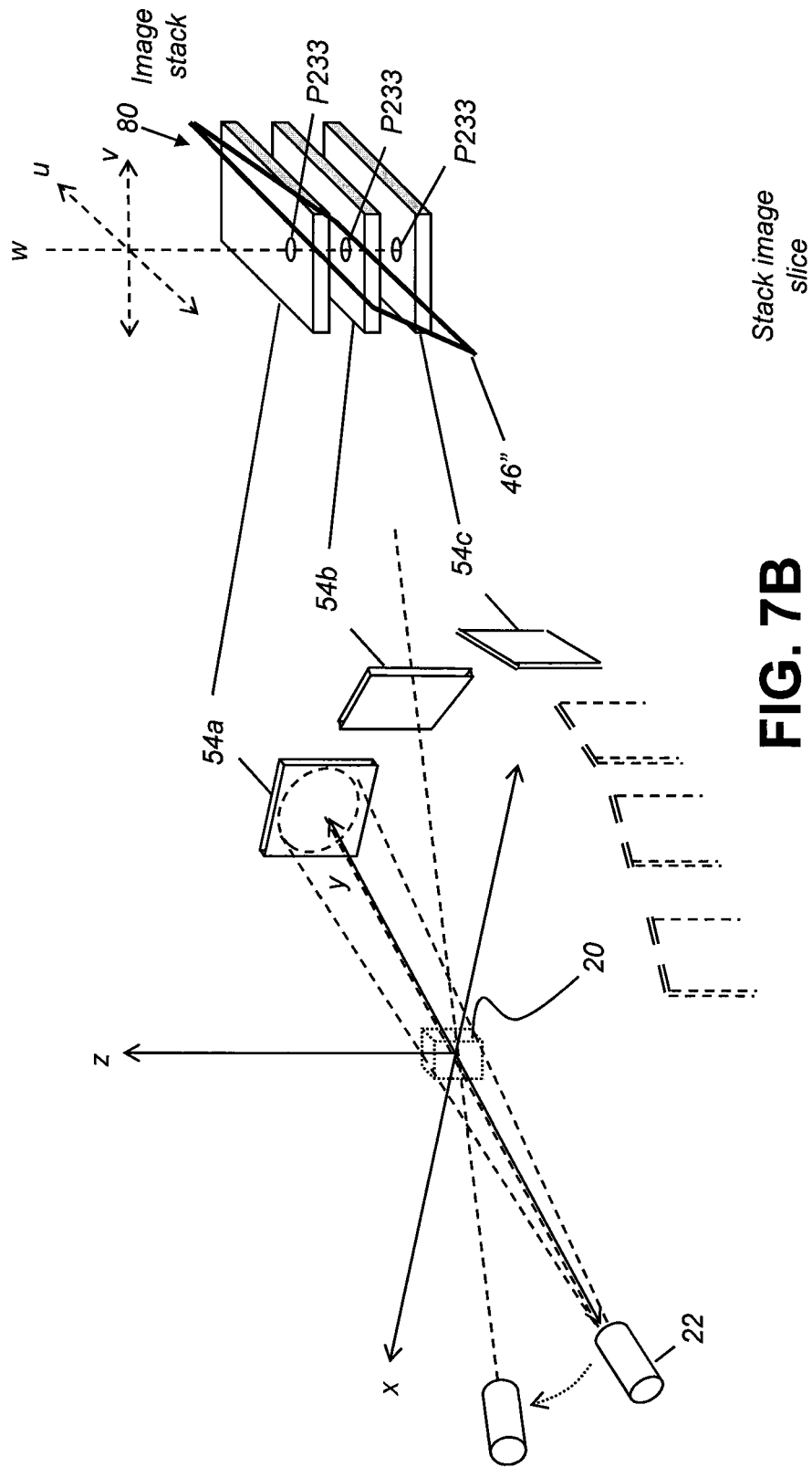

Again, the term "stack image slice", numbered 46, is preferably used herein to describe a 2-D image slice that is obtained as an orthogonal slice from image stack 80. However, embodiments of the application are not intended to be so limited, for example, a single stack image slice 46', 46" as shown in FIGS. 7A-7B can be in a plane or direction that is not parallel to the obtained projection images of the image stack. In one embodiment, single stack image slice 46', 46" may not pass though the entire image stack. Such exemplary embodiments can used multi-planar image processing analysis to perform segmentation or automatic 3-D metal segmentation by considering multiple or sequential stack image slices 46', 46". In one embodiment, not all projection images 54 are used in the image stack 80.

Data Replacement Step S330

In data replacement step S330 of FIG. 3, a 3-D filling method is employed in order to replace data in the segmented metal feature from step S320. According to an embodiment of the application, inpainting may be performed to faithfully propagate structural content for voxels that are within the region being replaced. Inpainting is a process, known to those skilled in the image processing arts, that replaces image data that is known to be, or likely to be, lost or corrupted in some way, such as pixels or voxels considered to be in the "shadow" of nearby metal or other highly dense components. Inpainting generates replacement pixels or voxels that provide likely image content. Inpainting and similar techniques familiar to those skilled in the imaging arts help to provide consistency between successive image slices and, when properly applied, can help to reduce artifacts related to metal and highly dense objects that lie within less dense bone and tissue. Inpainting is described, for example, in an article by M. Bertalmio, G. Sapiro, V. Caselles, and C. Ballester, entitled "Image inpainting", *In Proc. SIGGRAPH'00*, New Orleans, USA, pages 417-424, 2000.

Conversion Step S340

Conversion step S340 of FIG. 3 takes the stacked 3-D volume data that has been processed in steps S310, S320, and S330 and converts this data back to 2-D projection views at corresponding scan angles. This generates modified set of projection images 84. Among its benefits, modified set of projection images 84 has reduced metal object content and is thus less likely to cause artifacts or other problems upon subsequent 3-D reconstruction.

Combination Step S350

Combination step S350 in the FIG. 3 sequence takes the modified set of projection images 84 and, for each corresponding scan angle, combines the modified projection image obtained from steps S310, S320, S330, and S340 with the original projection image in set of projection images 60. In one embodiment, the modified projection image obtained from steps S310, S320, S330, and S340 can be subtracted from the original projection image in the set of projection images 60. The subtraction result is then optionally scaled, based on an empirically generated model. This generates corrected set of projection images 88 for subsequent reconstruction in step S360 and generation of 3-D volume image 90.

Methods for combining data from modified set of projection images 84 with the original 2-D set of projection images 60 are described, for example, in commonly assigned U.S. patent application Ser. No. 13/234,472 entitled "METAL ARTIFACTS REDUCTION FOR CONE BEAM CT" by Yang et al., incorporated by reference herein in its entirety. 3-D volume image reconstruction using 2-D projection images can be performed using any of a number of methods known to those skilled in the imaging arts.

The 3-D volume image 90 reconstruction based on processed projection images has been shown to provide noticeable image quality improvement, with overall reduction of metal artifacts.

The following have been noted:

(i) Significant reduction of fine streak artifacts induced by the edge-gradient at the boundaries between the metal object and surrounding tissue. This effect is achieved by replacing image elements for the metal object with image elements having a compensating density value.

(ii) Beam hardening correction can be conducted on the original metal shadow segment prior to processing using the exemplary apparatus and/or method embodiments herein so as to make body part information more consistent with information viewed from other projection angles that do not have the metal object in the path.

(iii) For less dense implants, exemplary apparatus and/or method embodiments herein can help to obtain more information about nearby tissue in the shadow of the metal object.

(iv) For very dense implants, processing by exemplary apparatus and/or method embodiments according to the application show a dramatic reduction in dark band artifacts.

(v) Implant material characteristics under different kVp conditions can be recorded and used for other implants and objects of the same material. It should be noted that obtaining shape and size information for the metal object is unnecessary when using exemplary apparatus and/or method embodiments described herein; the material itself must be identified, however.

Certain exemplary apparatus and/or method embodiments of the application process the original 2-D projection data, rather than processing the 3-D volume data that is generated from the 2-D projection data. This can simplify processing and help to avoid problems such as potential mismatch between surrogate data (which is forward projected from the reconstruction volume) and the surrounding originally measured data, as is a problem encountered when using the conventional quasi-iterative based FBP approach noted in the background section.

Consistent with one embodiment of the present disclosure, the present disclosure utilizes a computer program with stored instructions that perform on image data accessed from an electronic memory. As can be appreciated by those skilled in the image processing arts, a computer program of an embodiment of the application can be utilized by a suitable, general-purpose computer system, such as a personal computer or workstation. However, many other types of computer systems can be used to execute the computer program of the application, including networked processors. The computer program for performing the method of the application may be stored in a computer readable storage medium. This medium may comprise, for example; magnetic storage media such as a magnetic disk such as a hard drive or removable device or magnetic tape; optical storage media such as an optical disc, optical tape, or machine readable bar code; solid state electronic storage devices such as random access memory (RAM), or read only memory (ROM); or any other physical device or medium employed to store a computer program. The computer program for performing the method of the application may also be stored on computer readable storage medium that is connected to the image processor by way of the internet or other communication medium. Those skilled in the art will readily recognize that the equivalent of such a computer program product may also be constructed in hardware.

It should be noted that the term "memory", equivalent to "computer-accessible memory" in the context of the application, can refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Displaying an image requires memory storage. Display data, for example, is typically stored in a temporary storage buffer that is directly associated with a display device and is periodically refreshed as needed in order to provide displayed data. This temporary storage buffer can also be considered to be a memory, as the term is used in the application. Memory is also used as the data workspace for executing and storing intermediate and final results of calculations and other processing. Computer-accessible memory can be volatile, non-volatile, or a hybrid combination of volatile and non-volatile types.

It will be understood that the computer program product of the application may make use of various image manipulation algorithms and processes that are well known. It will be further understood that the computer program product embodiment of the application may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present disclosure, are not specifically shown or described herein and may be selected from such algorithms, systems, hardware, components and elements known in the art.

In one embodiment, a method for reducing metal artifacts in a volume generated from volume image data of a subject, can include obtaining a first plurality of two-dimensional radiographic images of the subject on an image detector, wherein each of the images is obtained with the detector and a radiation source at a different scan angle relative to the subject; arranging the image data from the first plurality of two-dimensional radiographic images so that corresponding pixel data from the detector is in register for each of the images in the first plurality of two-dimensional radiographic images; segmenting pixels that represent metal objects from the obtained image data by a repeated process of obtaining a two-dimensional image slice from the image data, wherein the obtained two-dimensional image slice has image pixel data from each of the first plurality of radiographic images, and processing the obtained two-dimensional image slice to identify metal features; replacing data for at least some of the segmented pixels using inpainting to generate a second plurality of modified two-dimensional radiographic images; combining the second plurality of modified two-dimensional radiographic images with the first plurality of two-dimensional radiographic images of the subject to form a third plurality of combined images; reconstructing a three-dimensional volume image according to the third plurality of combined images using filtered back projection; and displaying, storing, or transmitting an image slice from the reconstructed three-dimensional volume image. In one embodiment, the method is executed at least in part on a computer.

The invention has been described in detail, and may have been described with particular reference to a suitable or presently preferred embodiment, but it will be understood that variations and modifications can be effected within the spirit and scope of the invention. For example, exemplary embodiments can pre-process (e.g., reduce or bin) image data that is correlated to form an image stack. In one embodiment, not all the information in the 2-D projection images 54 is used (e.g., the metal is localized in a subset of the projection images). Thus, multiple planes can be processed, however each pixel in each projection image is not processed in one of the image stack slices 46 that are taken from image stack 80. The presently disclosed exemplary embodiments are therefore considered in all respects to be illustrative and not restrictive. The scope of the invention is indicated by the appended claims, and all changes that come within the meaning and range of equivalents thereof are intended to be embraced therein.

Exemplary embodiments according to the application can include various features described herein (individually or in combination).

While the invention has been illustrated with respect to one or more implementations, alterations and/or modifications can be made to the illustrated examples without departing from the spirit and scope of the appended claims. In addition, while a particular feature of the invention can have been disclosed with respect to one of several implementations, such feature can be combined with one or more other features of the other implementations as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by the following claims, and all changes that come within the meaning and range of equivalents thereof are intended to be embraced therein.

What is claimed is:

1. A method for processing volume image data of a subject, the method executed at least in part on a computer, comprising:

obtaining two-dimensional radiographic images of the subject on an image detector, where each of the two-dimensional radiographic images are obtained with the image detector and a radiation source at a different scan angle relative to the subject;

stacking image data from a first plurality of the two-dimensional radiographic images in an image stack so that corresponding pixel data from the detector is in register using a characteristic sinusoidal pattern for each of the first plurality of the two-dimensional radiographic images in the image stack;

segmenting pixels that represent metal objects from said each of the first plurality of the two-dimensional radiographic images of the image stack by a repeated process of obtaining an image stack slice from the image stack in a direction that is orthogonal to the obtained two-dimensional radiographic images and processing the obtained image stack slice;

replacing data for at least some of the segmented pixels to generate a second plurality of modified two-dimensional radiographic images with a reduced amount of the pixels that represent metal objects;

combining the second plurality of modified two-dimensional radiographic images with the first plurality of two-dimensional radiographic images of the subject to form a third plurality of corrected two-dimensional radiographic images;

reconstructing a three-dimensional volume image using the third plurality of corrected two-dimensional radiographic images; and displaying, storing, or transmitting an image slice from the three-dimensional volume image.

2. The method of claim 1 wherein replacing the data for at least some of the segmented pixels comprises using image inpainting.

3. The method of claim 1 wherein segmenting pixels comprises automatically identifying seed pixels in one or more images obtained from the image stack.

4. The method of claim 1 wherein segmenting pixels comprises obtaining operator input for seed pixels for each of the metal objects and non-metal objects in one or more images obtained from the image stack.

5. The method of claim 1 wherein the first plurality of two-dimensional radiographic images are obtained from a cone-beam computed tomography system or obtained from a fan-beam computed tomography system, wherein the reconstructing the three-dimensional volume image comprises using filtered back projection.

6. The method of claim 1 wherein the combining further comprises subtracting data from the first plurality of two-dimensional image data.

7. The method of claim 1, where segmenting pixels that represent metal objects from the image stack uses a repeated process of obtaining a two-dimensional image slice from the image stack, wherein the obtained two-dimensional image slice has image pixel data from a plurality of the first plurality of radiographic images, and processing the obtained two-dimensional image slice to identify metal features.

8. The method of claim 7, where the replacing the data for at least some of the segmented pixels comprises using image inpainting.

9. A method for processing volume image data of a subject, the method executed at least in part on a computer, comprising:

obtaining a first plurality of two-dimensional radiographic images of the subject on an image detector, wherein each of the two-dimensional radiographic images is obtained with the image detector and a radiation source at a different scan angle relative to the subject;

arranging image data from the first plurality of two-dimensional radiographic images in an image stack so that corresponding pixel data from the detector is in register for each of the first plurality of two-dimensional radiographic images in the image stack;

segmenting pixels that represent metal objects from said each of the first plurality of the two-dimensional radiographic images of the image stack by a repeated process of obtaining an image stack slice from the image stack in a direction that is not parallel to the obtained two-dimensional radiographic images and processing the obtained image stack slice;

modifying data for at least some of the segmented pixels to generate a modified image stack with a reduced metal object content;

converting the modified image stack back into a second plurality of two-dimensional radiographic images at the different scan angles relative to the subject;

reconstructing a three-dimensional volume image according to the second plurality of two-dimensional radiographic images; and displaying, storing, or transmitting an image slice from the reconstructed three-dimensional volume image.

10. The method of claim 9, wherein modifying the data for at least some of the segmented pixels comprises using image inpainting, and wherein reconstructing the three-dimensional volume image comprises using filtered back projection.

11. The method of claim 9, wherein segmenting pixels comprises automatically identifying seed pixels for each of the metal objects, bone objects and tissue objects in an image obtained from the image stack.

12. The method of claim 9, wherein processing the obtained image stack slice comprises identifying pixels associated with metal features.

13. A method for processing volume image data of a subject, the method executed at least in part on a computer, comprising:

obtaining two-dimensional radiographic images of the subject on an image detector, where the two-dimensional radiographic images are obtained with the image detector and a radiation source at a different scan angle relative to the subject;

arranging image data from a first plurality of the two-dimensional radiographic images in an image stack so that corresponding pixel data from the detector is in register for each of the first plurality of two-dimensional radiographic images in the image stack;

re-arranging the image stack by a repeated process of obtaining an image stack slice from said each of the first plurality of the two-dimensional radiographic images of the image stack in a direction that is not parallel to the obtained two-dimensional radiographic images to form a second image stack;

replacing data for at least some pixels that represent metal objects in the second image stack by processing image stack slices in the second image stack;

obtaining a second plurality of modified two-dimensional radiographic images by obtaining a second image stack slice from the modified second image stack in a plane parallel to the obtained two-dimensional radiographic images;

combining some of the second plurality of modified two-dimensional radiographic images with the first plurality of two-dimensional radiographic images of the subject to form a third plurality of combined images;

reconstructing a three-dimensional volume image according to the third plurality of combined images; and displaying, storing, or transmitting an image slice from the reconstructed three-dimensional volume image.

14. The method of claim 13, where re-arranging the image stack executes a repeated process of obtaining the image stack slice from the image stack in a plane that is orthogonal to the plane of the obtained two-dimensional radiographic images in the image stack and processing the obtained image stack slice.

* * * * *